(12) United States Patent
Chen et al.

(10) Patent No.: US 12,357,390 B2
(45) Date of Patent: Jul. 15, 2025

(54) OPTIMAL MIDLINE SETTING METHOD FOR SURGICAL PLANNING AND NAVIGATION SYSTEM

(71) Applicants: Meng-Yen Chen, Tainan (TW); Chen-Jung Chang, Tainan (TW)

(72) Inventors: Meng-Yen Chen, Tainan (TW); Chen-Jung Chang, Tainan (TW)

( * ) Notice: Subject to any disclaimer, the term of this patent is extended or adjusted under 35 U.S.C. 154(b) by 168 days.

(21) Appl. No.: 18/341,040

(22) Filed: Jun. 26, 2023

(65) Prior Publication Data
US 2024/0423718 A1 Dec. 26, 2024

(51) Int. Cl.
*A61B 34/10* (2016.01)
*A61B 34/20* (2016.01)

(52) U.S. Cl.
CPC ............ *A61B 34/10* (2016.02); *A61B 34/20* (2016.02); *A61B 2034/105* (2016.02); *A61B 2034/107* (2016.02)

(58) Field of Classification Search
CPC ... A61B 34/10; A61B 34/20; A61B 2034/105; A61B 2034/107; A61B 34/25; A61B 5/1075; G06T 7/0012; G06T 2207/30016
See application file for complete search history.

(56) References Cited

U.S. PATENT DOCUMENTS

| | | | |
|---|---|---|---|
| 9,630,026 B2* | 4/2017 | Froehlich | A61N 5/1082 |
| 9,741,114 B2* | 8/2017 | Varkuti | G16H 50/50 |
| 10,592,581 B2* | 3/2020 | Thomson | G06F 17/10 |
| 11,861,828 B2* | 1/2024 | Nguyen | G06T 7/0012 |
| 2021/0338106 A1* | 11/2021 | Howard | A61B 5/1075 |
| 2023/0068121 A1* | 3/2023 | Lindeman | A61B 34/25 |

OTHER PUBLICATIONS

Brainlab elements Trajectory Planning Version 2.5. Software User Guide Revision 1.0 (Year: 2019).*
Computer-Aided Craniomaxillofacial Surgery Planning. Cheng, Yuan. National University of Singapore (Year: 2011).*

* cited by examiner

*Primary Examiner* — Joel Lamprecht
(74) *Attorney, Agent, or Firm* — Best & Flanagan LLP (57) ABSTRACT

An optimal midline setting method for a surgical planning and navigation system is implemented by a computer device of the surgical planning and navigation system according to operating instructions, and the method includes: creating a skull 3D model and an auxiliary object corresponding to the skull 3D model, and the auxiliary object correlating to an optimal symmetry plane generated through a quantifiable symmetry criterion method; overlapping and aligning the skull 3D model and the auxiliary object to a central position, and the optimal symmetry plane displayed in at least two of a top view section, a side view section and a front view section of the skull 3D model; and setting an optimal midline on the skull 3D model along the optimal symmetry plane for the surgical planning and navigation system to operate according to the optimal midline.

2 Claims, 9 Drawing Sheets
(5 of 9 Drawing Sheet(s) Filed in Color)

OPTIMAL MIDLINE SETTING METHOD FOR SURGICAL PLANNING AND NAVIGATION SYSTEM

BACKGROUND OF THE INVENTION

1. Field of the Invention

The present invention relates to a symmetry plane setting method, and particularly to an optimal midline setting method for a surgical planning and navigation system.

2. Description of the Related Art

Figure 9:
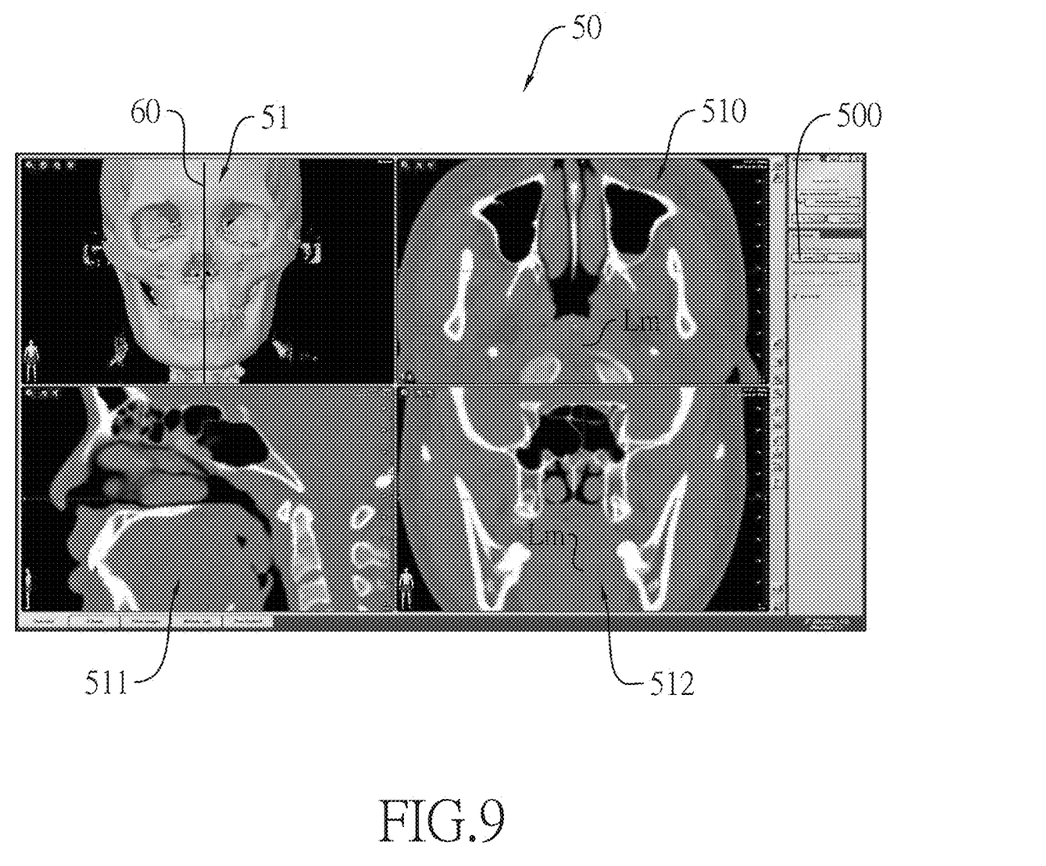
FIG. 9 is a schematic diagram of an operating interface presented by a conventional surgical planning and navigation system.

In general, a surgical planning and navigation system can measure relative positions of tissue characteristics of patients and surgical instruments through different positioning methods such as optical or magnetic force. The surgical planning and navigation system then shows real-time images for surgeons to review. In this way, the surgeons can correctly move surgical instruments to a target position to perform or simulate a surgery according to the real-time images presented by the surgical planning and navigation system. Referring to FIG. 9, FIG. 9 shows an operation interface 50 of the surgical planning and navigation system named Brainlab® currently available in the market. The operation interface 50 displays a skull 3D model 51 in one of multiple windows, and displays a top view section 510, a side view section 511 and a front view section 512 corresponding to the skull 3D model 51 in the other three windows.

There is an align button 500 in the operation interface 50 of the surgical planning and navigation system of Brainlab®. The align button 500 provides a midline setting function. A surgeon respectively selects and moves the positions of the top view section 510, the side view section 511 and/or the front view section 512 in each respective window according to experience. When one of the top view section 510, the side view section view section 511 and the front view section 510 is moved, the other two sections and the skull 3D model 51 are also simultaneously moved. When the top view section 510, the side view section 511 and the front view section 510 are moved to a central position in each respective window as estimated by the surgeon, where the surgeon refers to as a central reference line Lm displayed in each respective window to determine the central position, the surgeon then clicks the align button 500 to execute a midline setting function. The midline 60 will be displayed on the skull 3D model 51 to indicate a central line of a patient's face. For example, the surgeon can operate the surgical planning and navigation system to perform a surgery or a surgery simulation according to the midline 60 for improving the bilateral symmetry of the patient's face.

As mentioned earlier above, the midline 60 is manually determined according to subjective judgment and experience of the surgeon that operates the surgical planning and navigation system in a computer device. However, the manual setting method is time-consuming, and patients' individual differences may cause deviations in anatomical structures shown in the top view section 510, the side view section 511 and the front view section 510, thereby leading to a deviation of the midline 60. When the midline 60 deviates, the surgery or the surgery simulation will be directly affected, and the bilateral symmetry of the patient's face will not be effectively improved.

SUMMARY OF THE INVENTION

In view of this, a main purpose of the present invention is to provide an embodiment of an optimal midline setting method for a surgical planning and navigation system, in order to improve shortcomings of high time consumption and inaccuracy of a manual midline setting method in the related art.

An optimal midline setting method for a surgical planning and navigation system is implemented by a computer device of the surgical planning and navigation system according to operating instructions, and the method includes:

creating a skull 3D model and an auxiliary object corresponding to the skull 3D model, and the auxiliary object correlating to an optimal symmetry plane generated through a quantifiable symmetry criterion method, wherein the skull 3D model and the auxiliary object are displayed on a monitor;

overlapping and aligning the skull 3D model and the auxiliary object to a central position according to the operating instructions, and the optimal symmetry plane displayed in at least two of a top view section, a side view section and a front view section of the skull 3D model; and setting an optimal midline on the skull 3D model along the optimal symmetry plane for the surgical planning and navigation system to operate according to the optimal midline.

Firstly, overlapping and aligning the auxiliary object which present the optimal symmetry plane and the skull 3D model each other through the optimal midline setting method of the present invention to locate a position of the optimal symmetry plane on the skull 3D model, and then taking the position of the optimal symmetry plane as an objective reference standard for setting the optimal midline.

In this way, with the optimal symmetry plane as a basis, the surgeon no longer needs to merely rely on an anatomical structure, theoretically located in a middle position, as a reference for setting a midline. Due to individual anatomical differences and errors in point selection, the midline manually selected will have errors. In addition, adjusting an axial direction of each section on a computer screen to generate the midline is very time-consuming, and said process needs to be completed on a planning computer before a surgery. In general, errors of setting the midline are usually discovered after the surgery is completed. Performing the surgery again just to correct the errors of midline-setting will likely incur disturbance and disputes. The method of the present invention uses a function of setting a midline of the surgical planning and navigation system, such that the optimal midline can be set more accurately according to the optimal symmetry plane. The optimal midline generated by the present invention is used as an objective reference standard, and accuracy of the optimal midline is higher than midline of the related art, such that the optimal midline of the present invention can truly reflect a central line of a patient's head, neck and even the axial skeleton. As a result, when operating the surgical planning and navigation system with the optimal midline to perform a surgery or a surgery simulation, the left-right symmetry of the patient's face will be effectively improved.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
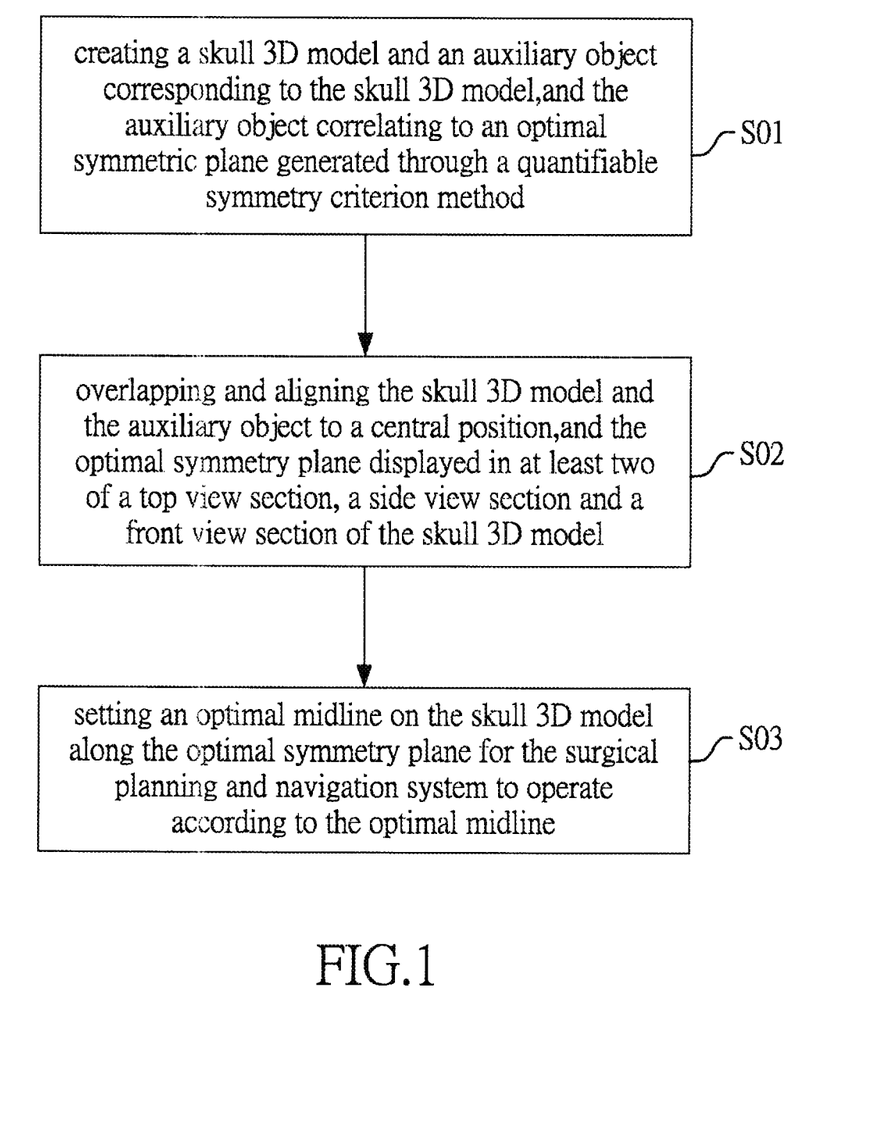
FIG. 1 is a flow chart of an embodiment of an optimal midline setting method for a surgical planning and navigation system of the present invention.

The present invention is an optimal midline setting method for a surgical planning and navigation system. In an embodiment of the present invention, the surgical planning and navigation system uses the surgical planning and navigation system of Brainlab® as an example, but is not limited thereto. Basic operations of the surgical planning and navigation system of Brainlab® can be referred to in the description of the related art as discussed above and will not be repeated herein. The surgical planning and navigation system includes a computer device (not shown in the figure), and the operation of the surgical planning and navigation functions are implemented by the computer device. The setting method of the present invention is implemented through the computer device of the surgical planning and navigation system according to operating commands of a user such as a surgeon. Referring to FIG. 1, the present invention includes the following steps.

Figure 2:
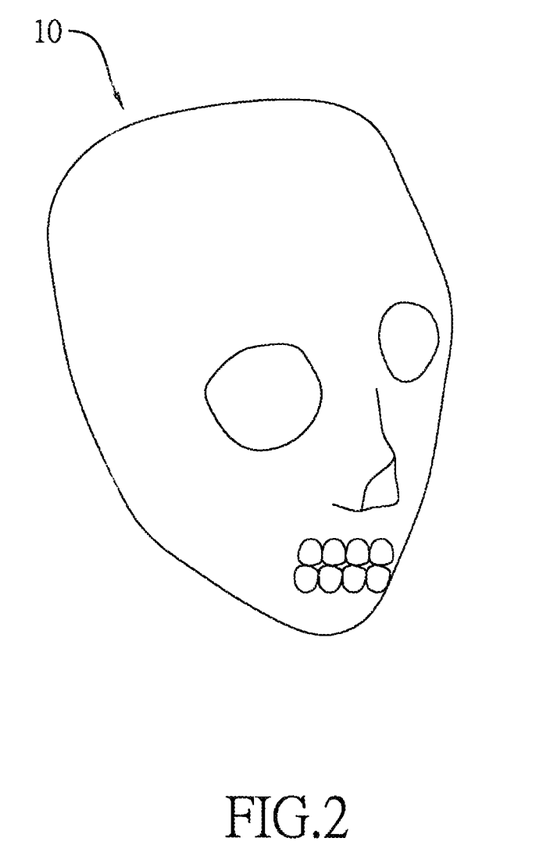
FIG. 2 is a schematic diagram of a skull 3D model of the present invention.

Step S01: creating a skull 3D model and an auxiliary object corresponding to the skull 3D model, and the auxiliary object correlating to an optimal symmetry plane generated through a quantifiable symmetry criterion method. Referring to FIG. 2, the skull 3D model 10 in this step can be a 3D image generated through a Computed Tomography (CT) or a Magnetic Resonance Imaging (MRI), and the skull 3D model is inputted into the computer device of the surgical planning and navigation system. The skull 3D model 10 includes different parts of the patient's skull bones, such as the zygomatic bone, the maxillary bone and the mandible bone, etc. Another computer device (hereinafter referred to as a second computer device) generates the auxiliary object according to the skull 3D model 10 and imports the auxiliary object into the computer device of the surgical planning and navigation system. The generation method of the auxiliary object is described as follows, wherein the file of the auxiliary object can be pre-stored in a computer-readable recording medium (such as a memory or a memory card), and the computer-readable recording medium is connected to the computer device of the surgical planning and navigation system. The computer device of the surgical planning and navigation system is able to access the file of the auxiliary object. Alternatively, the computer device of the surgical planning and navigation system and the second computer device can be wired or wirelessly connected to transmit the file of the auxiliary object.

Before a surgery, the skull 3D model 10 may be pre-input to the second computer device, so that the second computer device implements a quantifiable symmetry criterion method on the skull 3D model 10. The quantifiable symmetry criterion method mainly includes steps a to c. The step a is inputting a digitized medical image data into a computer device for calculating. The digitized medical image is the skull 3D model 10 in the embodiment of the present invention. The step b is performing image processing with an algorithm including an error equation of the gray level value to obtain optimal parameters. The step c is performing image processing according to said optimal parameters to obtain an Optimal Symmetry Plane (OSP) of the digitized medical image (i.e., the skull 3D model 10).

Figure 3:
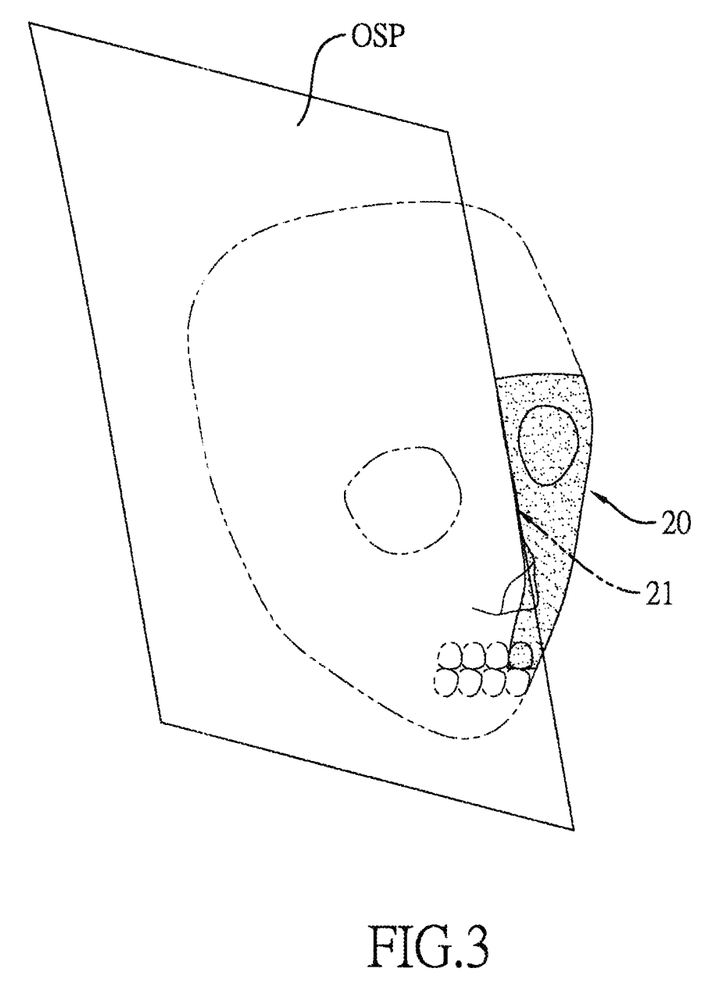
FIG. 3 is a schematic diagram of an auxiliary object generated according to an optimal symmetry plane of the present invention.

The second computer device can remove a partial structure of the skull 3D model 10 through a 3D image editing software and according to user's operating instructions to form an embodiment of the auxiliary object. The file format of the auxiliary object can be a .STL file. After the partial structure of the skull 3D model is removed, either a left half skeleton 3D model or a right half skeleton 3D model corresponding to the skull 3D model 10 can be formed, and the zygomatic bone and the maxillary bone are included in the left half or the right half skeleton 3D model. An auxiliary object 20 shown in FIG. 3 is the left half skeleton 3D model. The auxiliary object 20 includes at least one section, and the at least one section includes a sagittal section 21. The sagittal section 21 is overlapped with the optimal symmetry plane OSP generated by the quantifiable symmetry criterion method.

Step S02: Overlapping and aligning the skull 3D model and the auxiliary object to a central position, and the optimal symmetry plane is displayed in at least two of a top view section 130, a side view section 131 and a front view section 132 of the skull 3D model. In an embodiment, color formats of the skull 3D model 10 and the auxiliary object 20 are different from each other. As the computer device of the surgical planning and navigation system has been established with the skull 3D model 10 and auxiliary object 20, the skull 3D model 10 and auxiliary object 20 can be displayed in a monitor of the surgical planning and navigation system, wherein the monitor is connected to the computer device of the surgical planning and navigation system. When the skull 3D model 10 and the auxiliary object 20 are inputted into the computer device of the surgical planning and navigation system, the skull 3D model 10 and the auxiliary object 20 may be distributed in different positions on the monitor. Therefore, the computer device of the surgical planning and navigation system can overlap and align the skull 3D model 10 and auxiliary object 20 according to the user's operating instructions. For example, the user can operate a mouse and examine the monitor to move and overlap the auxiliary object 20 to a corresponding position of the skull 3D model, and make a contour of the auxiliary object 20 align with a contour of the skull 3D model 10 to complete overlapping and aligning of the skull 3D model 10 and auxiliary object 20.

Figure 4:
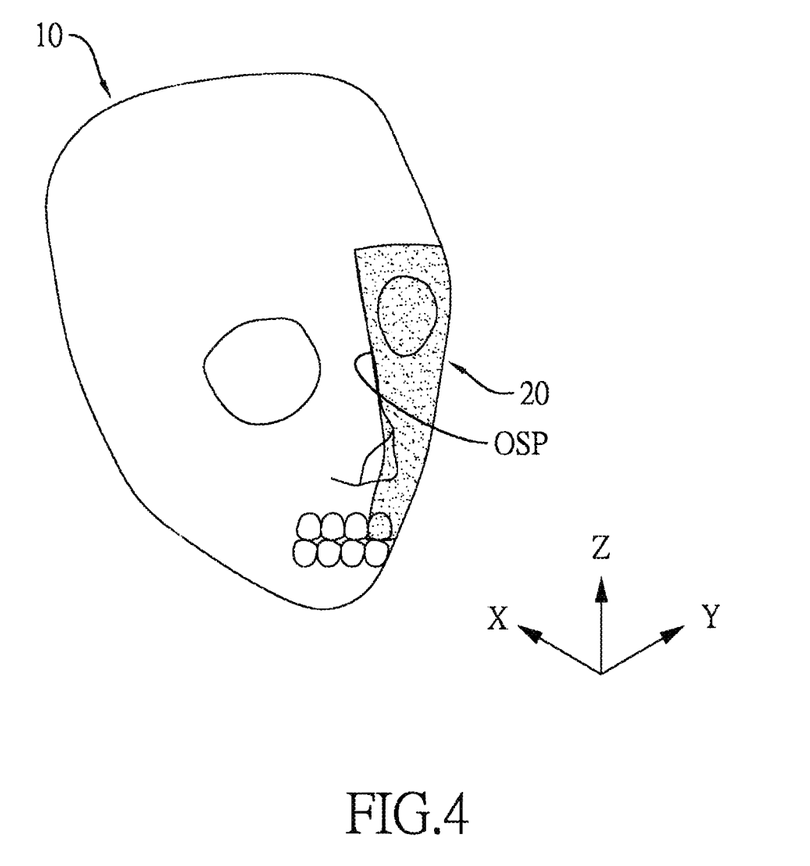
FIG. 4 is a schematic diagram of the skull 3D model and the auxiliary object overlapping and aligning with each other of the present invention.

In a state that the skull 3D model 10 and the auxiliary object 20 have been overlapped and aligned, because the color formats of the skull 3D model 10 and the auxiliary object 20 are different from each other, a color contrast between the skull 3D model 10 and the auxiliary object 20 is formed. For example, a surface color format of the skull 3D model 10 can be based on white, and a color format of the auxiliary object 20 can be non-white, transparent or fluorescent. Referring to FIGS. 3 and 4, the auxiliary object 20 is stippled and the skull 3D model 10 is not stippled to present different color formats of the skull 3D model 10 and auxiliary object 20. If viewed from the frontal projection of the skull 3D model 10 and the auxiliary object 20 (a Y-Z plane shown in FIG. 4), the optimal symmetry plane OSP appears at the junction of the skull 3D model 10 and auxiliary object 20. In this way, the user can directly distinguish the optimal symmetry plane OSP at the junction of the skull 3D model 10 and the auxiliary object 20 on the monitor.

Figure 5:
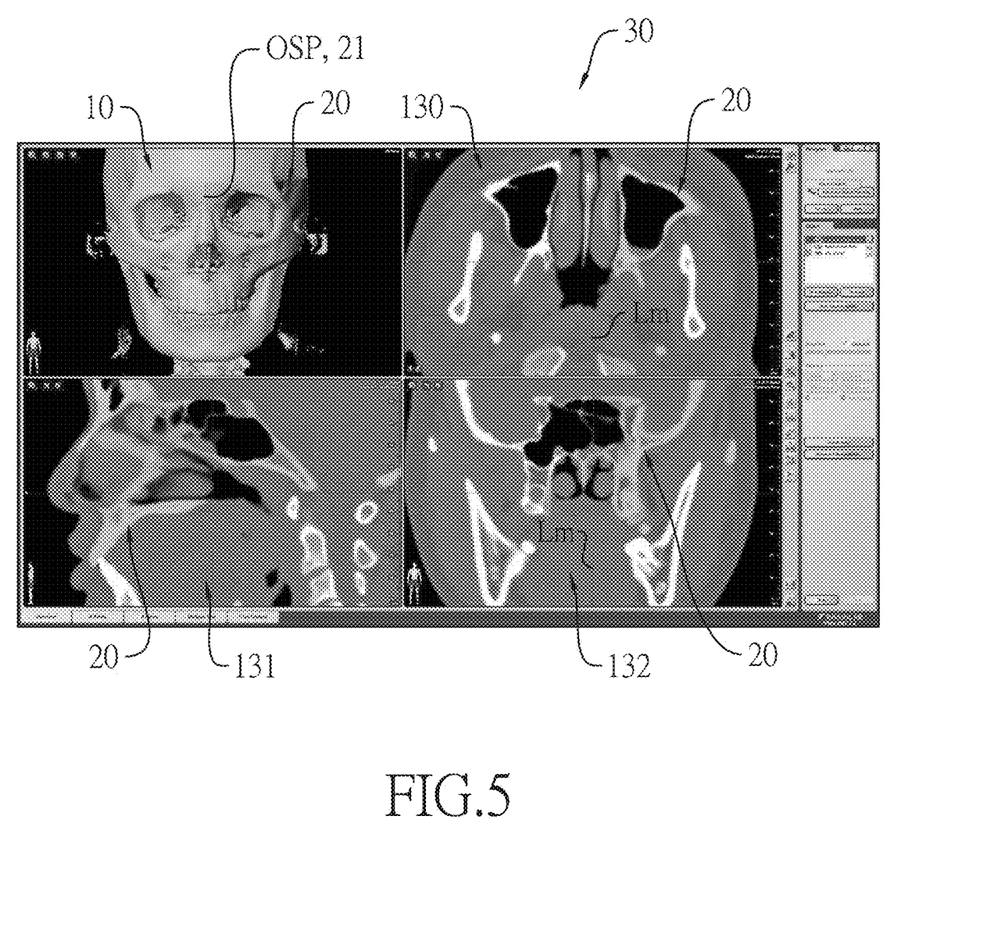
FIG. 5 is a schematic diagram of an operating interface presented by the surgical planning and navigation system of the present invention.

FIG. 5 is an operating interface 30 of the computer device of the surgical planning and navigation system, and the operating interface 30 is displayed on the monitor aforementioned. After the skull 3D model 10 and the auxiliary object 20 have been overlapped and aligned, the color format of the auxiliary object 20 is green as shown in FIG. 5 and contrasts with the color of the skull 3D model 10. The optimal symmetry plane OSP (i.e., the sagittal section 21 of the auxiliary object 20) appears at the junction of the skull 3D model 10 and the auxiliary object 20. Windows and descriptions in the operating interface 30 as shown in FIG. 5 can refer to FIG. 9 and will not be repeated herein. Briefly, the user respectively selects and moves the position of the skull 3D model 10, the top view section 130, the side view section 131, the front view section 132 and the auxiliary object 20 in each respective window to perform overlap and alignment. For example, the user can firstly move the position of the auxiliary object 20 to align the sagittal section 21 with a central reference line Lm of each respective window, and then move the top view section 130, the side view section 131 and/or the front view section 132 in each respective window to overlap and align with the auxiliary object 20. After the skull 3D model 10 and the auxiliary object 20 have been overlapped and aligned, green parts in the windows of the top view section 130, the side view section 131 and the front view section 132 are the auxiliary object 20. Therefore, the user can view the position of the optimal symmetry plane OSP, wherein the top view section 130, the side view section 131 and the front view section 132 are at the central position of each respective window.

Step S03: Setting an optimal midline on the skull 3D model along the optimal symmetry plane for the surgical planning and navigation system to operate according to the optimal midline. The optimal symmetry plane OSP has been displayed at the junction of the auxiliary object 20 and the skull 3D model 10, the top view section 130, the side view section 131 and the front view section 132 in the step S02, so the user can directly and respectively set the optimal midline in each respective window of the top view section 130, the side view section 131 and/or the front view section 132 according to the position of the optimal symmetry plane OSP. As a result, the optimal midline overlaps the optimal symmetry plane OSP located at an edge of the auxiliary object 20, wherein the computer device of the surgical planning and navigation system sets the optimal midline on the skull 3D model 10 along the optimal symmetry plane OSP according to the user's operating instructions.

Figure 6:
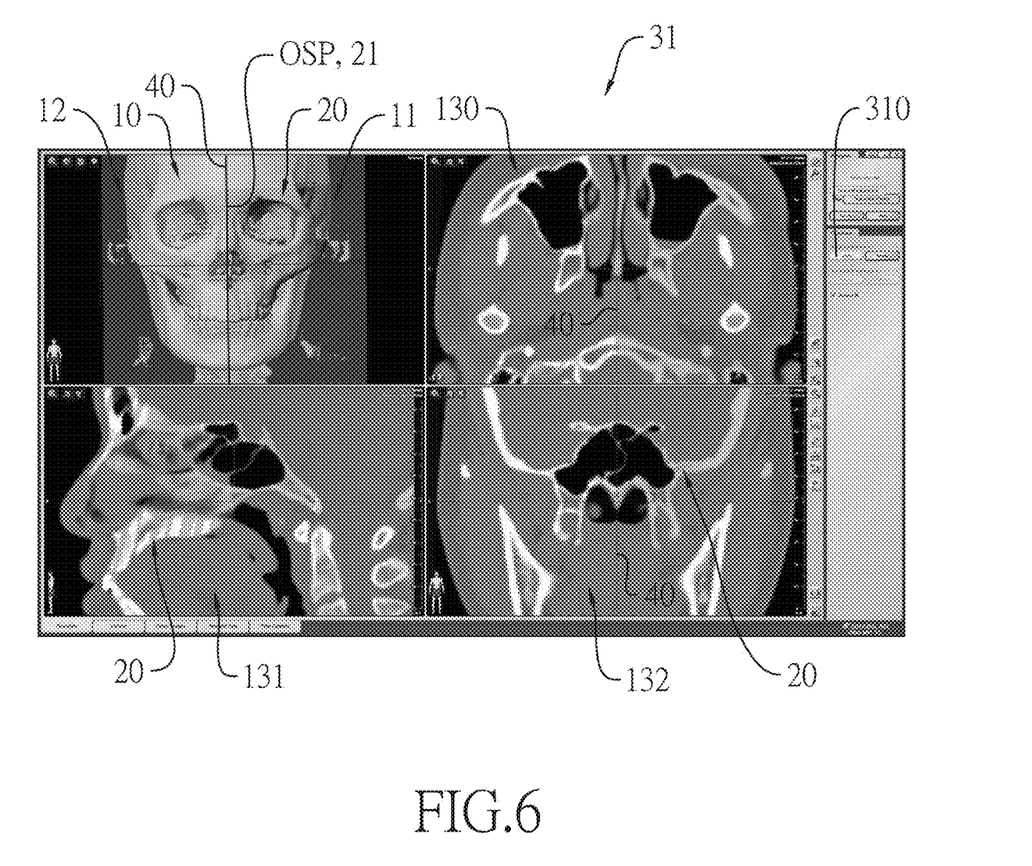
FIG. 6 is a schematic diagram of an operating interface presented by the surgical planning and navigation system of the present invention.

In an embodiment of the present invention, an operating interface 31 shown in FIG. 6 has an align button 310 for the user to set the optimal midline 40. When the top view section 130, the side view section 131 and the front view section 132 are moved to the central position of each respective window, the align button 310 is allowed to be clicked by a user to perform an aligning function. When the computer device of the surgical planning and navigation system sets the optimal midline 40 according to the instructions, the optimal midline 40 can overlap the optimal symmetry plane OSP. As a result, the optimal symmetry plane OSP is set as the optimal midline 40 on the surgical planning and navigation system. The computer device of the surgical planning and navigation system operates according to the optimal midline 40, and the optimal midline 40 serves as an objective reference to provide functions of pre-surgery planning of each bone and reference for intraoperative placement.

For example, referring to FIG. 6, in a surgery or a pre-surgery simulation, the computer of the surgical planning and navigation system can divide the skull 3D model 10 into a left half 11 and a right half 12 according to the optimal midline 40 and mirror the right half 12 to the left half 11 to make the right half 12 overlap the left half 11, wherein the color format of the mirrored right half 12 can be translucent. In this way, a skeletal structure difference between the mirrored right half 12 and the original left half 11 can be shown through overlapping images to be a reference for surgeons to perform the surgery or the simulation of the surgery.

The auxiliary object 20 in the aforementioned embodiment is taking half side skeletal 3D models as an example, and the auxiliary object 20 can also basically consist of points, lines or surfaces in other embodiments.

Figure 7:
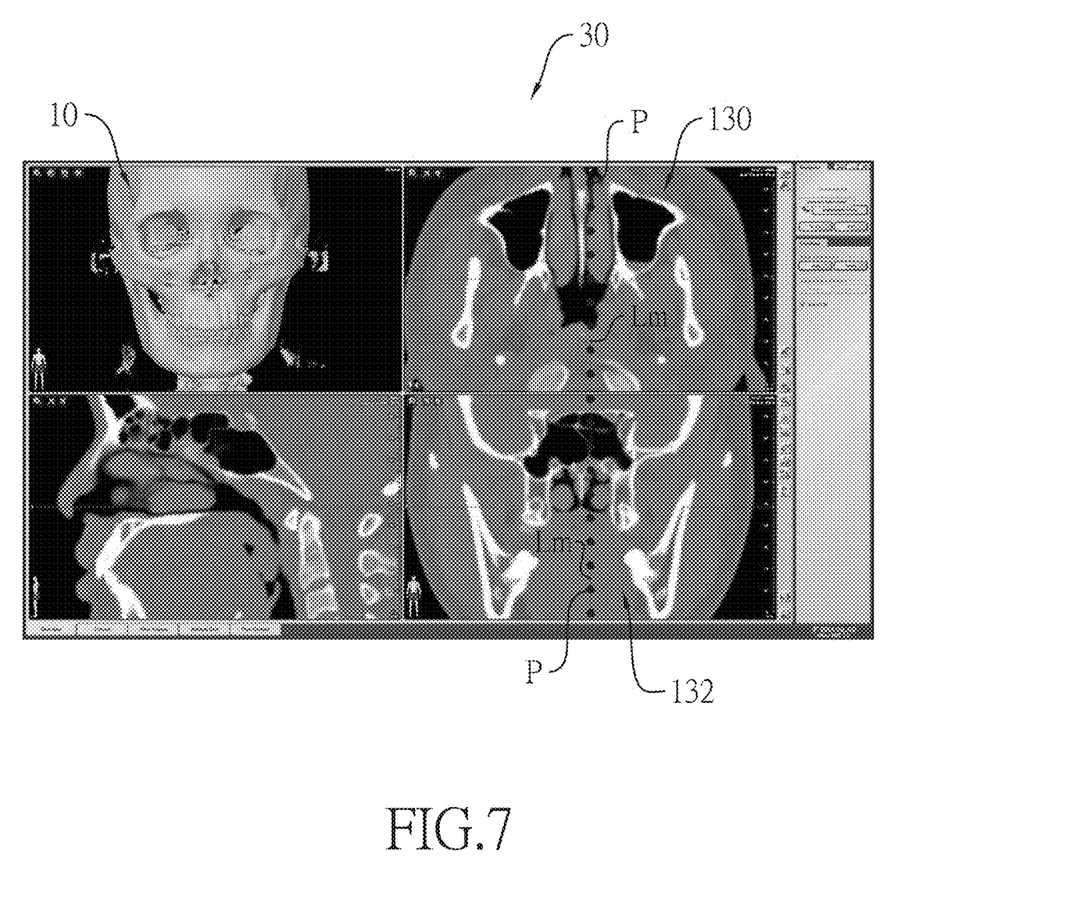
FIG. 7 is a schematic diagram of an operating interface presented by the surgical planning and navigation system of the present invention.

In an embodiment, the auxiliary object 20 may basically consist of points. In the step S01, the second computer device can capture coordinates of a plurality of points of the optimal symmetry plane OSP through the 3D image editing software and according to user's operating instructions, and compose the auxiliary object 20 by the plurality of points. In other words, the auxiliary object 20 may include a plurality of points distributed along the optimal symmetry plane OSP. In the step S02, referring to FIG. 7, the plurality of points P will be displayed in the windows of at least the top view section 130 and the front view section 132. When the skull 3D model 10 and the auxiliary object 20 have been overlapped and aligned to the central position, the plurality of points P can be also aligned with the central reference line Lm of each respective window.

Figure 8:
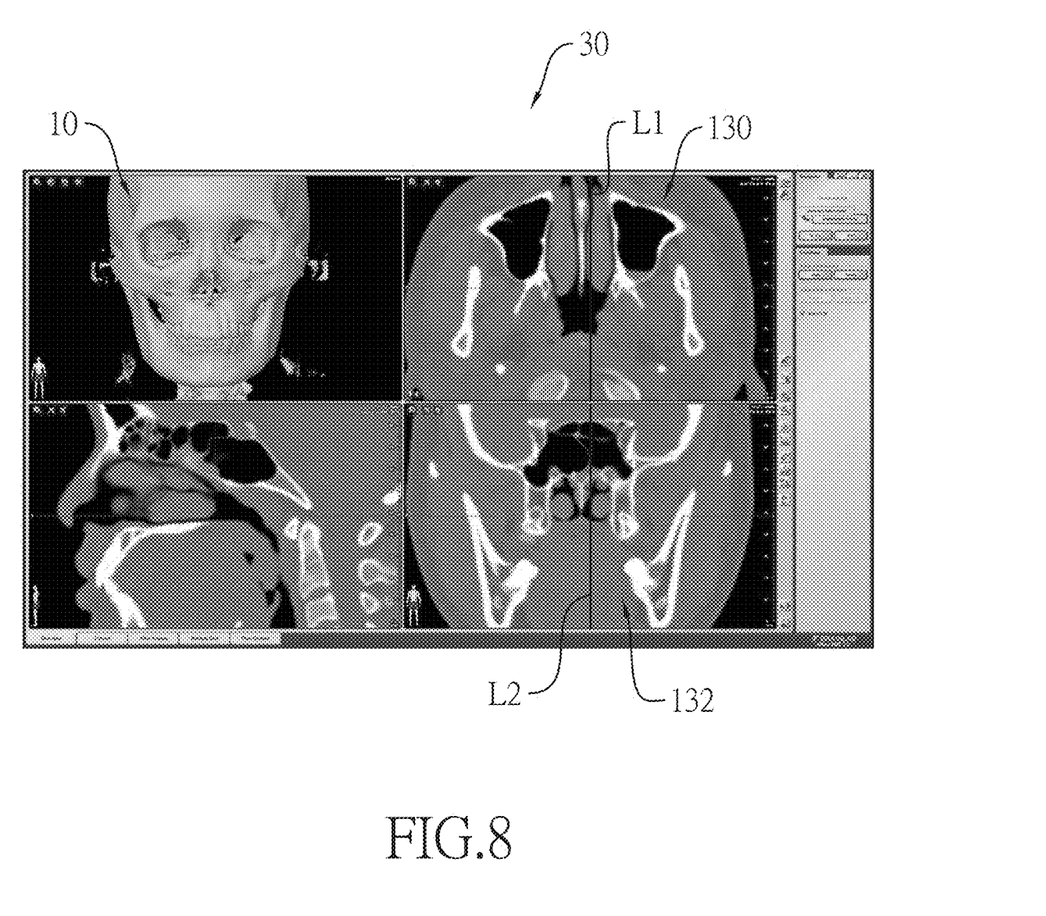
FIG. 8 is a schematic diagram of an operating interface presented by the surgical planning and navigation system of the present invention.

In another embodiment, the auxiliary object 20 may basically consist of lines. In the step S01, the second computer device can capture a program data of a sagittal axis line and a longitudinal axis line of the optimal symmetry plane OSP through the 3D image editing software and according to user's operating instructions, and compose the auxiliary object 20 by the sagittal axis line and the longitudinal axis line. In other words, the auxiliary object 20 may include the sagittal axis line and the longitudinal axis line along the optimal symmetry plane OSP. In the step S02, referring to FIG. 8, the sagittal axis line and the longitudinal axis line will be displayed in the windows of at least the top view section 130 and the front view section 132. When the skull 3D model 10 and the auxiliary object 20 have been overlapped and aligned to the central position, the sagittal axis line and the longitudinal axis line can be also aligned with the central reference line Lm of each respective window.

In another embodiment, the auxiliary object 20 may basically consist of planes. The planes can be deduced according to types of the points and lines aforementioned. In the step S01, the second computer device can capture a program data of the sagittal section 21 of the auxiliary object 20 through the 3D image editing software and according to user's operating instructions to sever as a reference plane. In other words, the reference plane overlaps the optimal symmetry plane OSP and composes the auxiliary object 20. In the step S02, the reference plane will be displayed in the windows of at least the top view section 130 and the front view section 132. When the skull 3D model 10 and the auxiliary object 20 have been overlapped and aligned to the central position, the reference plane can be also aligned with the central reference line Lm of the each respective window.

Specifically, when the auxiliary object 20 is inputted into the computer of the surgical planning and navigation system, the computer can establish the auxiliary object 20 and the skull 3D model 10 in a same coordinate system through a coordinate transformation, such that the optimal symmetry plane OSP can be correspondingly displayed in the skull 3D model 10, the top view section 130, the side view section 131 and the front view section 132. Since the coordinate transformation is common knowledge in image processing technology, the coordinate transformation is not to be described in detail hereinafter.

In view of the above, the user can save time to set the optimal midline 40 through the optimal midline setting method of the present invention. On the other hand, the optimal midline 40 is generated according to the optimal symmetry plane OSP and thus can truly and objectively reflect the central line of the patient's face. During a surgery or a surgery simulation with the optimal midline 40, the left-right symmetry of the patient's face will be effectively improved.

What is claimed is:

1. An optimal midline setting method for a surgical planning and navigation system, implemented by a computer device of the surgical planning and navigation system according to operating instructions, the method including:
    creating a skull 3D model and an auxiliary object and displaying the skull 3D model and the auxiliary object on a monitor connected to the computer device; wherein the skull 3D model and the auxiliary object are inputted into the computer device and in a same coordinate system through a coordinate transformation by the computer device; wherein the skull 3D model is a 3D image generated through Computed Tomography or Magnetic Resonance Imaging; and wherein the auxiliary object is movable and correlates to an optimal symmetry plane generated through a quantifiable symmetry criterion method on the skull 3D model and is selected from one of the following:
        a left or right half skeleton 3D model of the skull 3D model, wherein a sagittal section of the left or right half skeleton 3D model is overlapped with the optimal symmetry plane;
        a plurality of points distributed along the optimal symmetry plane;
        a sagittal axis line and a longitudinal axis line along the optimal symmetry plane; and
        a reference plane overlapped with the optimal symmetry plane;
    overlapping and aligning the skull 3D model and the auxiliary object to a central position according to user's operating instructions for the optimal symmetry plane to appear at a junction of the skull 3D model and the auxiliary object, wherein the optimal symmetry plane is displayed in at least two of a top view section, a side view section, and a front view section of the skull 3D model on the monitor; and
    setting an optimal midline on the skull 3D model along the optimal symmetry plane by the computer device when an align button of an operating interface is clicked for the surgical planning and navigation system to operate according to the optimal midline.

2. The optimal midline setting method as claimed in claim 1, wherein the skull 3D model and the auxiliary object are different from each other in color formats.

* * * * *